US010437959B2

United States Patent
Dyell et al.

(10) Patent No.: US 10,437,959 B2
(45) Date of Patent: Oct. 8, 2019

(54) PATIENT SENSOR DATA EXCHANGE SYSTEMS AND METHODS

(71) Applicant: NANTHEALTH, INC., Culver City, CA (US)

(72) Inventors: David Dyell, Panama City, FL (US); Christopher Rogowski, Newtown Square, PA (US); Scott Kahler, Tuscaloosa, AL (US); Jennifer Milan, Westminister, CO (US)

(73) Assignee: NANTHEALTH, INC., Culver City, CA (US)

( * ) Notice: Subject to any disclaimer, the term of this patent is extended or adjusted under 35 U.S.C. 154(b) by 0 days.

(21) Appl. No.: 14/835,714

(22) Filed: Aug. 26, 2015

(65) Prior Publication Data

US 2016/0058390 A1     Mar. 3, 2016

Related U.S. Application Data

(60) Provisional application No. 62/043,340, filed on Aug. 28, 2014.

(51) Int. Cl.
*G06F 19/00* (2018.01)

(52) U.S. Cl.
CPC ........ *G06F 19/3418* (2013.01); *G06F 19/328* (2013.01)

(58) Field of Classification Search
CPC ............. G06F 19/3418; G06F 19/3412; G06F 19/3406; G06F 19/345; G06F 19/323; G06F 19/321; A61B 5/0022; A61B 5/1112; A61B 5/0002; G06Q 50/22; G06Q 50/24; G06Q 10/10; A61M 16/00; A61M 16/0051; Y10S 128/92
See application file for complete search history.

(56) References Cited

U.S. PATENT DOCUMENTS

| 6,738,671 | B2 | 5/2004 | Christophersom et al. |
|---|---|---|---|
| 7,181,283 | B2 | 2/2007 | Hettrick et al. |
| 7,229,409 | B2 | 6/2007 | Ito et al. |
| 8,255,240 | B2 | 8/2012 | O'Hanlon et al. |

(Continued)

FOREIGN PATENT DOCUMENTS

| WO | 9838909 | 9/1998 |
|---|---|---|
| WO | 02051354 | 7/2002 |
| WO | 2008116295 | 10/2008 |

*Primary Examiner* — Nabil H Syed
*Assistant Examiner* — Cal J Eustaquio
(74) *Attorney, Agent, or Firm* — Stetina Brunda Garred and Brucker

(57) ABSTRACT

A system for patient data exchange is provided and includes a plurality of sensors monitoring a patient according to a default sensor configuration, and a patient data exchange engine that receives a request comprising one or more parameters, identifies at least one applicable sensor from the plurality of sensors based on the one or more parameters, and reconfigures the at least one applicable sensor from the default sensor configuration to a different sensor configuration in accordance with the one or more parameters to generate applicable sensor data responsive to the request. In specific embodiments, the patient data exchange engine further computes a monetary value for the generated sensor data based at least on an attribute of the patient and an attribute of the sensor data.

21 Claims, 4 Drawing Sheets

(56) References Cited

U.S. PATENT DOCUMENTS

| | | | |
|---|---|---|---|
| 8,395,498 B2 | 3/2013 | Gaskill et al. | |
| 8,689,008 B2 | 4/2014 | Rangadass et al. | |
| 2002/0116226 A1* | 8/2002 | Auer | G06F 19/321 |
| | | | 705/3 |
| 2004/0215981 A1* | 10/2004 | Ricciardi | G06Q 10/10 |
| | | | 726/27 |
| 2006/0074722 A1 | 4/2006 | Chu | |
| 2006/0089541 A1* | 4/2006 | Braun | G06F 19/3418 |
| | | | 600/300 |
| 2006/0253066 A1* | 11/2006 | Zhang | A61B 5/0205 |
| | | | 604/65 |
| 2007/0135866 A1* | 6/2007 | Baker | A61B 5/0002 |
| | | | 607/60 |
| 2008/0164999 A1* | 7/2008 | Otto | A61B 5/0002 |
| | | | 340/540 |
| 2009/0058635 A1* | 3/2009 | Lalonde | A61N 1/37282 |
| | | | 340/539.11 |
| 2009/0118595 A1* | 5/2009 | Greiner | A61B 5/0006 |
| | | | 600/301 |
| 2010/0191542 A1 | 7/2010 | Monat et al. | |
| 2011/0077967 A1 | 3/2011 | Kapu et al. | |
| 2011/0102190 A1* | 5/2011 | Vaidyanathan | H04Q 9/00 |
| | | | 340/870.17 |
| 2011/0313787 A1 | 12/2011 | Rangadass et al. | |
| 2013/0054272 A1 | 2/2013 | Rangadass et al. | |
| 2013/0104890 A1* | 5/2013 | Steinhauer | A61M 16/00 |
| | | | 128/204.18 |
| 2013/0144653 A1 | 6/2013 | Poe et al. | |
| 2013/0166317 A1 | 6/2013 | Beardall et al. | |
| 2013/0259348 A1* | 10/2013 | Blum | G06T 9/00 |
| | | | 382/131 |
| 2013/0304496 A1 | 11/2013 | Rangadass | |
| 2013/0304512 A1 | 11/2013 | Seshadri et al. | |
| 2016/0154942 A1* | 6/2016 | Delisle | G06F 19/3406 |
| | | | 702/189 |

* cited by examiner

PATIENT SENSOR DATA EXCHANGE SYSTEMS AND METHODS

CROSS-REFERENCE TO RELATED APPLICATION

This application claims the benefit of priority under 35 U.S.C. § 119(e) to U.S. Provisional Patent Application Ser. No. 62/043,340, filed on Aug. 28, 2014 and entitled PATIENT SENSOR DATA EXCHANGE SYSTEMS AND METHODS, the disclosure of which is hereby incorporated by reference in its entirety.

TECHNICAL FIELD

This disclosure relates in general to the field of healthcare systems and, more particularly, to systems and methods related to patient sensor data exchanges.

BACKGROUND

The background description includes information that may be useful in understanding the present disclosure. It is not an admission that any of the information provided herein is prior art or relevant to the disclosure, or that any publication specifically or implicitly referenced is prior art.

Medical scientists and researchers often require large amounts of in-depth patient data to study different types of diseases and treatments therefor. Ideally, the scientists and researchers would like to constantly and continuously monitor patients having a set of desired attributes (e.g., a condition, a disease, receiving certain treatments, certain demographic traits, etc.) by collecting valuable data through sensors coupled to the patients. In the past, this is only possible in a hospital setting, which limits the availability of patient and the amount of data that can be collected.

Efforts have been made in providing better ways of collecting and redistributing electronic patient data. One of the efforts includes an automated patient health monitoring and management system that monitors and transmits patient data. Another effort includes a medical monitoring system that monitors and wirelessly transmits medical data of a patient in real-time. Other efforts toward improving this field of technology are directed to drug development for selective drug use with individual treatment responsive patients; procuring regulatory data from patients via medical measurement devices; providing medical services and related measurements through computerized means; managing security information associated with wireless patient communications; online health monitoring; providing home health care services; controlling implantable medical device parameters in response to atrial pressure attributes; and providing externally worn transceivers for use with implantable medical devices.

However, all these disclosed systems and/or methods require that the patients be identified before monitoring their data. In addition, the installation of associated sensors can be costly, which might not justify a one-time use, or use for only one study. Thus, there is still a need to improve on the patient data collection and redistribution systems.

Note that all publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

SUMMARY

A patient data exchange system comprises a plurality of sensors monitoring a patient according to a default sensor configuration, and a patient data exchange engine that receives a request comprising one or more parameters, identifies at least one applicable sensor from the plurality of sensors based on the one or more parameters, and reconfigures the at least one applicable sensor from the default sensor configuration to a different sensor configuration in accordance with the one or more parameters to generate applicable sensor data responsive to the request. In a specific embodiment, the default sensor configuration comprises a time-synchronization with another of the plurality of sensors. In some embodiments, the patient data exchange engine rejects the request if reconfiguring the applicable sensor defeats an original purpose of the at least one sensor. In some embodiments, the patient data exchange engine aggregates multiple streams of the sensor data associated with a plurality of patients sharing at least one attribute.

In some embodiments, the applicable sensor generates the corresponding sensor data at a first sampling rate according to the default sensor configuration, and the patient data exchange reconfigures the applicable sensor to have a second sampling rate according to the one or more parameters. In other embodiments, the patient data exchange engine reconfigures the applicable sensor to remove an identifier associated with the patient from the sensor data according to the one or more parameters.

In some embodiments, the patient data exchange engine further computes a monetary value for the generated sensor data based (among other factors) on an attribute of the patient and an attribute of the sensor data and further enables a transaction with respect to the generated sensor data using the computed monetary value. Examples of the attribute of the patient include a demographic attribute, a health condition of the patient, and a location of the patient. In some embodiments, the patient data exchange engine further computes the monetary value based on a rarity of the attribute among a plurality of patients. In some embodiments, the patient data exchange engine further derives a correlation between the health attribute and the one or more parameters of the request, and computes a monetary value for the request based on the determined rarity and the correlation.

In various embodiments, the patient data exchange engine provides a user access to the generated sensor data. The patient data exchange engine may further scrub (e.g., cleanse, censor, etc.) the generated sensor data to remove any information that can identify the patient before providing the user access to the generated sensor data. In some embodiments, the patient data exchange engine further compresses the generated sensor data before providing to the user.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Figure 1:
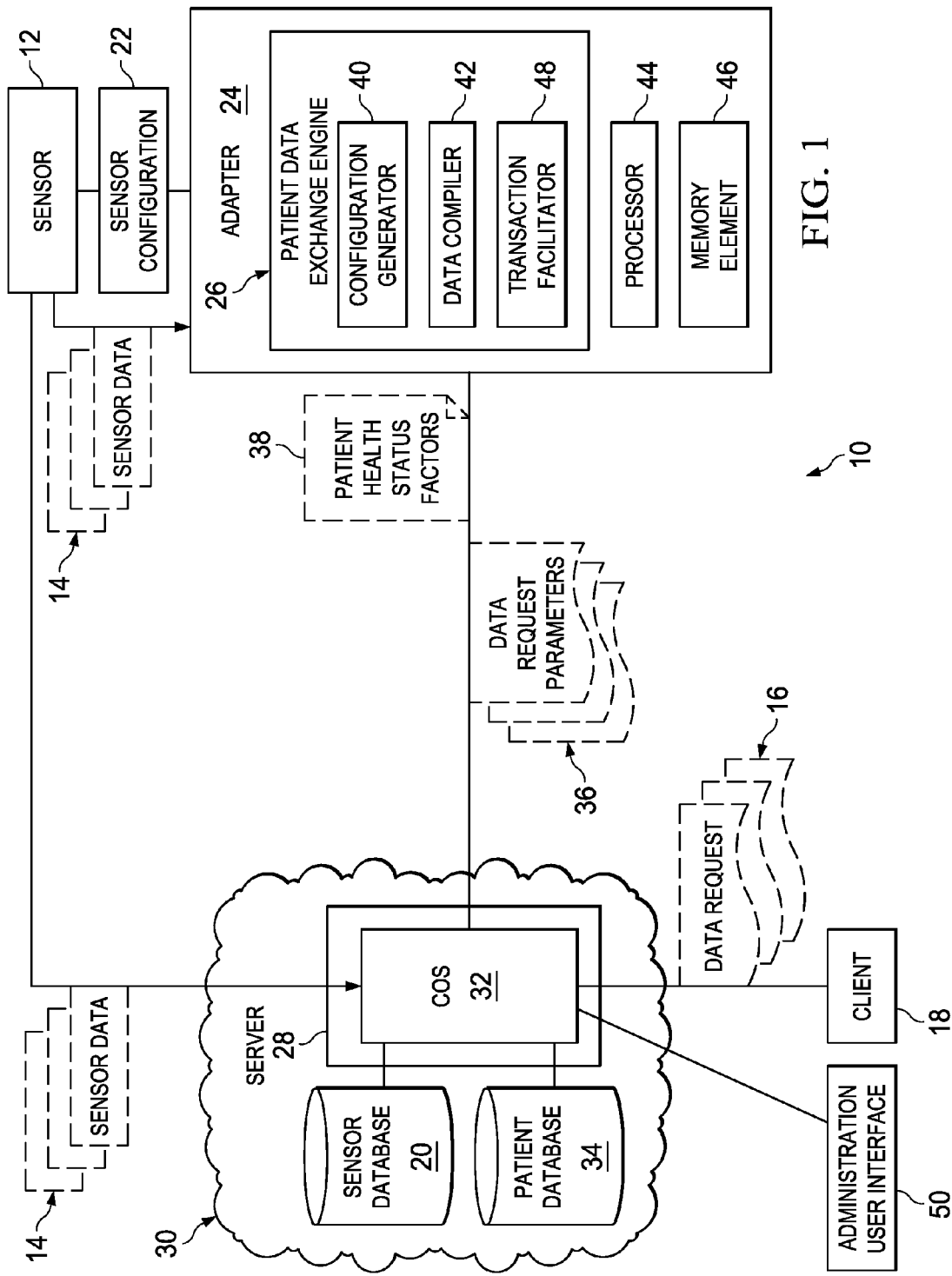
FIG. 1 is a simplified block diagram illustrating a system related to patient sensor data exchanges according to an example embodiment.

Turning to FIG. 1, FIG. 1 is a simplified block diagram illustrating a system 10 related to patient sensor data exchanges according to an example embodiment. The disclosure herein provides apparatus, systems and methods in which patients' sensor data is treated as a consumable product or data acquisition service that can be dynamically generated or transacted upon in a patient data exchange platform. In some embodiments, a patient data exchange system 10 is presented. Patient data exchange system 10 comprises one or more sensor 12 deployed and implemented on patients (not shown) for monitoring/measuring bodily conditions of the patients. Measurements taken by sensor 12 are converted into sensor data 14, to be processed (e.g., analyzed) by patient data exchange system 10.

In some embodiments, patient data exchange system 10 receives one or more data requests 16 for sensor data 14 from one or more clients 18. A user (e.g., medical scientists, researchers, doctors, healthcare providers, insurance entities, etc.) may operate client 18 appropriately, for example, through a suitable user interface (e.g., web service API, JSON, XML, etc.). In some embodiments, data request 16 comprises a set of parameters that specify attributes of the patients from which sensor data 14 is requested. The parameters can be associated with a particular patient's health status. For example, a medical scientist can request patient data exchange system 10 for sensor data 14 of patients who have been diagnosed with amyotrophic lateral sclerosis (ALS). Another data request 16 can be for sensor data 14 of patients who have been diagnosed with lung cancer. In some embodiments, patient data exchange system 10 allows client 18 to make more specific requirements (e.g., health condition plus demographic criteria, etc.) in data request 16. For example, data request 16 can request sensor data 14 of patients who are Caucasians and who have been diagnosed with lung cancer.

In response to data request 16, patient data exchange system 10 is programmed to identify at least one sensor 12 that can respond appropriately to data request 16 according to the parameters of the request. In some embodiments, patient data exchange system 10 is programmed to identify appropriate sensor 12 by comparing the parameters specified in data request 16 against various status parameters of sensors stored in sensor database 20. Patient data exchange system 10 is programmed to reconfigure identified sensor(s) 12 according to a sensor configuration 22 to generate sensor data 14 that is applicable to data request 16.

In some embodiments, patient data exchange system 10 converts generated sensor data 14 into a sensor stream, and enables a transaction with respect to the sensor stream. Patient data exchange system 10 of some embodiments computes a monetary value based on data request 16's parameters. Patient data exchange system 10 is programmed to enable the transaction based on the computed monetary value. Once the transaction is complete, patient data exchange system 10 is programmed to provide client 18 access to the generated sensor stream.

In the example embodiment of FIG. 1, an adapter 24 includes a patient data exchange engine 26. Adapter 24 is communicatively coupled to sensor 12 and to a server 28 in a network 30 that hosts a clinical operating system (cOS) 32. cOS 32 enables adapter 24 to interface with client 18, sensor database 20 and a patient database 34 in network 30. Sensor database 20 stores information about sensor 12 (and other sensors) within its sensor network, including sensor identifier that uniquely identifies sensor 12, sensor type, sensor capabilities, sensor configuration information, sensor status (e.g., online, collecting data, offline, etc.), etc. Patient database 34 stores information about the patients, including patient identifiers that uniquely identify each patient, patient names, patient genders, weight/height, and demographic information (e.g., ethnicity, age, etc.), current medical conditions (e.g., diseases, symptoms expressed in patient, etc.), medical condition history, current treatments, treatment history, etc. Although such patient specific data is available, it is contemplated that the patient identity can be kept secure or private. For example, the sensor stream could comprise ten heart rates from ten heart rate sensors where the ten heart rate sub-streams do not include patient identity information. This approach allows data scientists to analyze patient data as service, possibly in real-time, without compromising the patient's privacy.

In some embodiments, data request 16 from client 18 may be received at cOS 32, which then extracts relevant data request parameters 36 from data request 16 and transmits them to adapter 24. In some embodiments, cOS 32 may also transmit relevant patient health status factors 38 to adapter 24. A configuration generator 40 in adapter 24's patient data exchange engine 26 may generate sensor configuration 22 according to data request parameters 36 and patient health status factors 38. Sensor configuration 22 may be different from sensor 12's current configuration (e.g., as of the time of generating sensor configuration 22). In other words, sensor 12 may have a first sensor configuration, which may be different from a second sensor configuration, comprising sensor configuration 22.

Merely as an example, and not as a limitation, assume that sensor 12 is configured initially in a default sensor configuration to optimize collection of sensor data 14 for alerting the patient when the sensor's measurement on the patient indicates an escalating health condition. For example, the default configuration of sensor 12 specifies measurements on the patient at a certain default frequency (e.g., every 2 hours). Data request 16 from the patient's medical provider may request sensor data 14 associated with measurements on the patient at a different frequency (e.g., every 30 minutes). Consequently, sensor configuration 22 may specify a different measurement frequency than the default frequency for sensor 12.

In some embodiments, a data compiler 40 in adapter 24's patient data exchange engine 26 may generate instructions that configure sensor 12 to aggregate the data collected from the patient into a sensor stream according to data request parameters 36 and patient health status factors 38. The instructions may be added to sensor configuration 22 and transmitted to sensor 12. In some other embodiments, data compiler 40 may receive sensor data 14 and compile sensor data 14 into a data stream. In some embodiments, adapter 24 may store the updated sensor configuration 22 in sensor database 20 (e.g., through cOS 32). Adapter 24 may include a processor 44 and a memory element 46 for executing instructions associated with patient data exchange engine 26.

Sensor configuration 22 may reconfigure sensor 12 accordingly to cause sensor 12 to generate requested sensor data 14 according to data request 16. In some embodiments, sensor 12 may transmit sensor data 14 to cOS 32 directly. In other embodiments, sensor 12 may transmit sensor data 14 to adapter 24. In some embodiments, adapter 24 may pull sensor data 14 from sensor 12; in other embodiments, sensor 12 may push sensor data 14 to adapter 24. In some embodiments, adapter 24 may transmit sensor data 14 to cOS 32, for example, in a data stream. In other embodiments, adapter 24 may associate sensor data 14 with the patient (e.g., via a patient identifier) and store the associated data in patient database 34. cOS 32 may retrieve sensor data 14 from patient database 34 suitably. cOS 32 may send sensor data 14 (e.g., received from sensor 12, or adapter 24 or patient database 34) to client 18.

In some embodiments, data request parameters 36 and/or patient health status factors 38 may trigger a transaction facilitator 48 in adapter 24's patient data exchange engine 26. Transaction facilitator 48 may determine that a transaction should be completed in order for client 18 to receive requested sensor data 14. The transaction may comprise a commercial transaction, such as a buy-sell transaction, in which client 18 provides payment information and receives sensor data 14 in return. In other embodiments, the transaction may comprise an authenticated secure communication, for example, wherein sensor data 14 is to be transmitted in certain encrypted manner over secure tunnels to client 18. In yet other embodiments, the transaction may comprise a sequence of information exchange and related work (such as database lookup, database updating, etc.) that is treated as a unit for the purposes of satisfying data request 16 and for ensuring database integrity.

In some embodiments, information stored in patient database 34 and/or sensor database 20 can be manipulated (e.g., configured, selected, etc.) through an administration user interface 50. For example, an operator may select the type of information regarding sensor 12 to be stored in sensor database 20; the operator may select certain patient health information, such as patient health status factors 38 to be accessible by adapter 24 through cOS 32 from patient database 34.

Turning to the infrastructure of system 10, the network topology of network 30, including the network connecting to adapter 24 and/or sensor 12 can include any number of servers, routers, gateways, and other nodes inter-connected to form a large and complex network. A node may be any electronic device, client, server, peer, service, application, or other object capable of sending, receiving, or forwarding information over communications channels in a network. Elements of FIG. 1 may be coupled to one another through one or more interfaces employing any suitable connection (wired or wireless), which provides a viable pathway for electronic communications. Additionally, any one or more of these elements may be combined or removed from the architecture based on particular configuration needs.

System 10 may include a configuration capable of Transmission Control Protocol/Internet Protocol (TCP/IP) communications for the electronic transmission or reception of data packets in a network. Healthcare monitoring system 10 may also operate in conjunction with a User Datagram Protocol/Internet Protocol (UDP/IP) or any other suitable protocol, where appropriate and based on particular needs. In addition, gateways, routers, switches, and any other suitable nodes (physical or virtual) may be used to facilitate electronic communication between various nodes in the network.

Note that the numerical and letter designations assigned to the elements of FIG. 1 do not connote any type of hierarchy; the designations are arbitrary and have been used for purposes of teaching only. Such designations should not be construed in any way to limit their capabilities, functionalities, or applications in the potential environments that may benefit from the features of system 10. It should be understood that system 10 shown in FIG. 1 is simplified for ease of illustration.

The example network environment may be configured over a physical infrastructure that may include one or more networks and, further, may be configured in any form including, but not limited to, local area networks (LANs), wireless local area networks (WLANs), virtual local area networks (VLANs), metropolitan area networks (MANs), wide area networks (WANs), virtual private networks (VPNs), Intranet, Extranet, any other appropriate architecture or system, or any combination thereof that facilitates communications in a network.

In some embodiments, a communication link may represent any electronic link supporting a LAN environment such as, for example, cable, Ethernet, wireless technologies (e.g., IEEE 802.11x), ATM, fiber optics, etc. or any suitable combination thereof. In other embodiments, communication links may represent a remote connection through any appropriate medium (e.g., digital subscriber lines (DSL), telephone lines, T1 lines, T3 lines, wireless, satellite, fiber optics, cable, Ethernet, etc. or any combination thereof) and/or through any additional networks such as a wide area networks (e.g., the Internet).

In various embodiments, adapter 24 can include computer executable instructions stored on one or more non-transitory computer-readable media (e.g. hard drives, optical storage media, flash drives, ROM, RAM, etc.) that, when executed by one or more processors (e.g., processor 44), cause the processors to execute the functions and processes described herein. In some embodiments, some functionalities of adapter 24 may be implemented in a distributed manner, for example, at server 28 (through cOS 32). In some embodiments, adapter 24 may be generally compatible with any type of sensor, but may be specifically configured to interface with sensor 12. In other embodiments, adapter 24 may be configured to be compatible with only one type of sensor 12, for example, with different adapters for different sensor types.

In some embodiments, patient data exchange engine 26 may be implemented in firmware (e.g., specifically programmed application specific integrated circuit (ASIC), or field programmable gate array (FPGA), etc.) in adapter 24. In various embodiments, adapter 24 may be a standalone device that is coupled to sensor 12, for example, through a suitable interface (e.g., universal serial bus (USB) interface, Bluetooth™ interface, etc.) In other embodiments, adapter 24 may be integrated into sensor 12 (e.g., on a motherboard, etc.). In yet other embodiments, adapter 24 may be integrated with, or coupled to, a separate device, such as a mobile phone, computer, laptop, etc., which can communicate (e.g., wired or wirelessly) with sensor 12.

In various embodiments, cOS 32 may include a suitable operating system (or platform, or other appropriate software) that can federate various disparate data (e.g., from health providers, patients, sensors, other medical devices, etc.), aggregate the data in disparate formats to a uniform format (e.g., XML based format), and store the uniformly formatted data in a suitable data store (e.g., federated centralized database; data store for aggregated data) such as sensor database 20 and patient database 34 in network 30. cOS 32 may comprise a plurality of self-contained interconnected modules and service layers for connecting proprietary (and public) systems together and extracting and translating data therefrom to enable them to cooperate in a software ecosystem while allowing flexible connections with both existing and new applications. cOS 32 may offer a secure communication tunnel for adapter 24 to interface with sensor database 20 and patient database 34, and client 18. In some embodiments, cOS 32 can generally allow adapter 24 to interface with various other computer systems and/or adapters in network 30. Example suitable cOS 32 that can be suitably adapted for use with the disclosed subject matter includes those described by U.S. Pat. No. 8,689,008, and U.S. pre-grant publications 2011/0313787, 2013/0054272, 2013/0144653, 2013/0166317, 2013/0304512, and 2013/0304496, the disclosures of which are incorporated herein in their entireties.

In various embodiments, sensor 12 can include any suitable medical device that can monitor a health parameter of a patient, including pulse oximeters, galvanometers, blood pressure sensors, EKGs, EEGs, thermometers, or other types of sensors.

Figure 2:
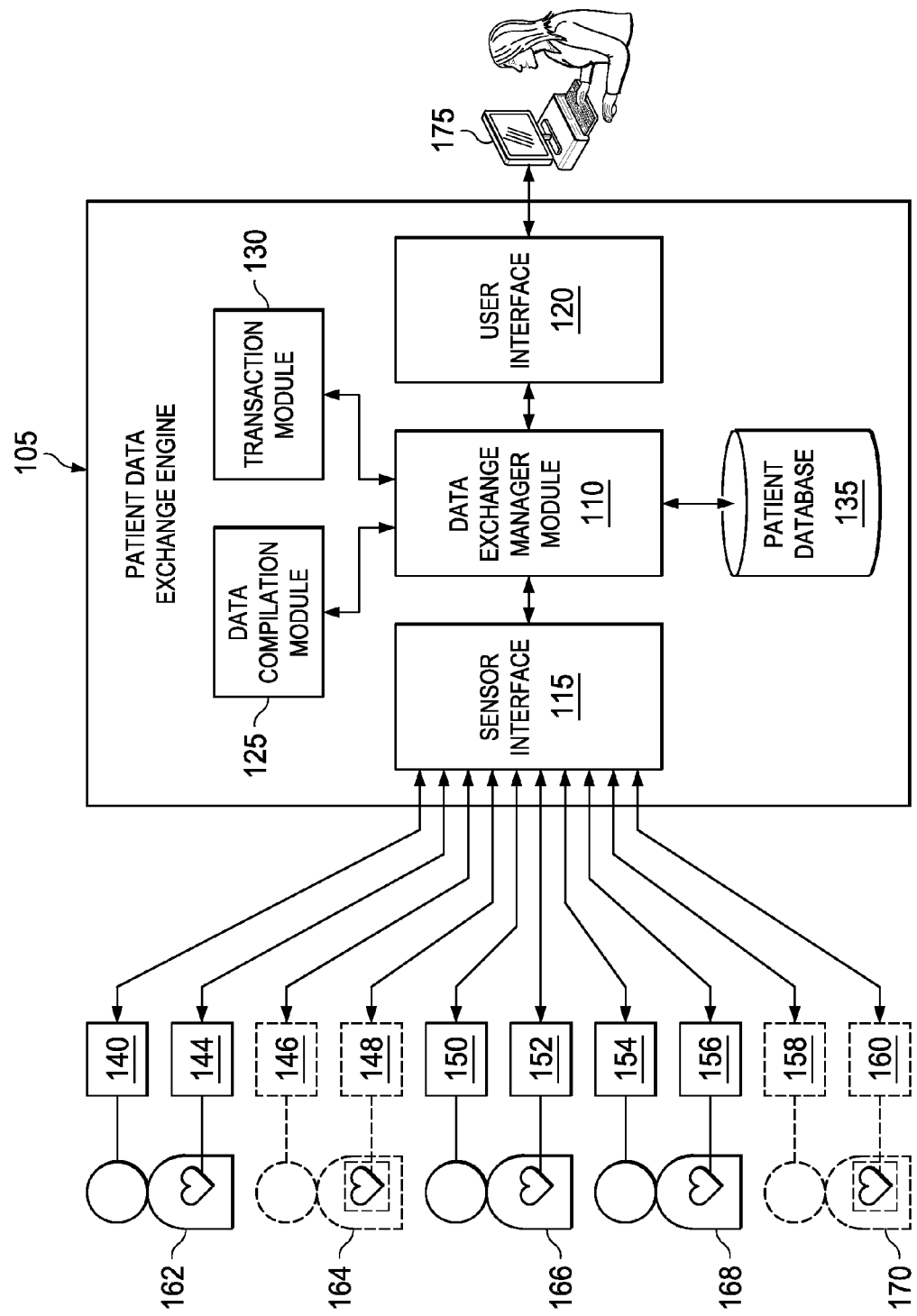
FIG. 2 is a simplified block diagram illustrating example details of the system according to an embodiment.

Turning to FIG. 2, FIG. 2 is a simplified block diagram illustrating an example patient data exchange system 100 of some embodiments. Patient data exchange system 100 comprises a patient data exchange engine 105 that is communicatively coupled with sensors 140-160 via a network (e.g., the Internet, a local area network, WiFi, ad-hoc, etc.). In some embodiments, patient data exchange engine 105 may be implemented in one or more mobile devices (e.g., tablet, smart phone, vehicle, etc.) or other computing device (e.g., laptop, kiosk, HBox™ device, appliance, etc.). Patient data exchange engine 105 includes a data exchange manager module 110, a sensor interface 115, a user interface 120, a data compilation module 125, and a transaction module 130. In some embodiments, data exchange manager module 110, sensor interface 115, user interface 120, data compilation module 125, and transaction module 130 can be implemented as software modules that when executed by one or more processing units (e.g., processors, processing cores, etc.) perform functionalities for patient data exchange engine 105.

Sensors 140-160 are attached to and/or associated with different patients 162-170. In one example embodiment, patients 162-170 comprise a heterogeneous group of patients, meaning that they have been diagnosed with different medical conditions (e.g., different diseases, etc.) and/or fall within different categories (e.g., demographic categories). In some embodiments, sensors 140-160 are configured to monitor and transmit patient data of patients 162-170, respectively, and send corresponding sensor data to patient data exchange engine 105. Sensors 140-160 are configured to monitor different aspects of patients 162-170. Merely as examples and not as limitations, sensors 140, 146, 150, 154, and 158 are configured to monitor body temperatures of patients 162-170; sensors 144, 148, 152, 156, and 160 are configured to monitor heart rates of patients 162-170. Example sensors can include pulse oximeters, galvanometers, blood pressure sensors, EKGs, EEGs, thermometers, or other types of sensors.

In some embodiments, sensors 140-160 are configured in a default sensor configuration. The default sensor configuration specifies settings of sensors 140-160 that can optimize collection of sensor data for an original purpose. For example, a patient might install a set of sensors to monitor his/her body condition (e.g., blood pressure, blood sugar content, etc.) so that the patient can receive an alert when the sensor data indicates an escalating condition. The original purpose of installing the sensors might give rise to a default setting of measuring at a certain frequency (e.g., every 2 hours, every 6 hours, etc.). In addition, the configuration may not require sensors 140-160 to be synchronized with each other for the original purpose.

In some embodiments, data exchange manager module 110 is programmed to actively retrieve (e.g., pulling) or passively receive (e.g., pushing) sensor data from sensors 140-160 via sensor interface 115. In some embodiments, patient data exchange engine 105 comprises or is communicatively coupled with a patient database 135. Patient database 135 may comprise a computing device that includes non-transitory data storage (e.g., a hard drive, a flash drive, RAM, etc.) and that is configured to store or retrieve data according to one or more schemas. After receiving the sensor data from sensors 140-160, data exchange manager module 110 may associate the sensor data to the corresponding patients and store the sensor data in patient database 135. In some embodiments, patient database 135 also stores information about patients 162-170, such as patient identifier that uniquely identifies the patient, patient name, patient gender, weight/height, and demographic information (e.g., ethnicity, age, etc.), current medical conditions (e.g., diseases, symptoms expressed in patient, etc.), medical condition history, current treatment, treatment history, etc.

In some embodiments, patient database 135 also stores information about sensors 140-160 within its sensor network, such as sensor identifier that uniquely identifies the sensor, sensor type, sensor capabilities, sensor configuration information, sensor status, etc. Data exchange manager module 110 can associate sensors 140-160 with their corresponding patients 162-170 by linking each sensor identifier with a patient identifier. For example, sensors 140 and 144 are associated with patient 162 because sensors 140 and 144 are configured to monitor body condition of patient 162, sensors 146 and 148 are associated with patient 164 because sensors 146 and 148 are configured to monitor body condition of patient 164, and so forth.

In some embodiments, patient data exchange engine 105 is also communicatively coupled with one or more clients 175 (e.g., user computer, laptop, mobile device, etc.) via the user interface 120 (e.g., an HTTP interface). Client 175 of some embodiments can include the entire or part of the patient data exchange engine 105. In other embodiments, patient data exchange engine 105 can be coupled with client 175 via a network (e.g., the Internet, a local area network, etc.). Client 175 can be any computing device such as a personal computer, a tablet, a mobile device, etc. In some of these embodiments, patient data exchange engine 105 through user interface 120 enables a user to make requests for sensor data via client 175.

In some embodiments, patient data exchange engine 105 enables the user to make requests for sensor data having a set of distinct attributes. For example, the user can make a request for sensor data associated with patients who have been diagnosed with amyotrophic lateral sclerosis (ALS). Another request can be for sensor data of patients who have been diagnosed with lung cancer. In some embodiments, patient data exchange system 10 allows the users to make more specific requirements (e.g., health condition plus demographic criteria, etc.) in the requests. For example, the user can request sensor data associated with patients who are Caucasians and who have been diagnosed with lung cancer. These attributes can be expressed in the form of a set of parameters included within the patient data request.

Upon receiving the patient data request that includes the set of parameters, data exchange manager module 110 sends the request to data compilation module 125 to compile or otherwise instantiate a sensor data stream that is applicable for the request based on the set of parameters. In some embodiments, data compilation module 125 identifies a subset of sensors 140-160 that are applicable to the request. For example, when the parameters specify patient data of patients who are Caucasians and who have been diagnosed with lung cancer, data compilation module 125 traverses the patient data in patient database 135 to identify patients that satisfy the criteria specified in the parameters. In this example, data compilation module 125 identifies that out of all patients 162-170, only patients 162, 166, and 168 are both Caucasians and diagnosed with lung cancer. Data compilation module 125 also identifies sensors 140, 144, 150, 152, 154, and 156 that are associated with patients 162, 166, and 168.

Although in this example, data compilation module 125 identifies (or selects) sensors 140, 144, 150, 152, 154, and 156 that are associated with the identified patients 162, 166, and 168 for the request, data compilation module 125 can be programmed to further select only a subset of sensors 140, 144, 150, 152, 154, and 156 based on the parameters as not all sensors may be applicable to the request in some cases. For example, patient data exchange engine 105 may select sensors that have the capabilities to fulfill the needs (e.g., sampling rate requirement, sensibility requirement, etc.) specified in the parameters, and ignore other sensors. Data exchange manager module 105 collects sensor data from identified sensors 140, 144, 150, 152, 154, and 156 and converts the sensor data into a sensor data stream. In some embodiments, patient data exchange engine 105 can collect the sensor data and convert the sensor data into the data stream indefinitely until the user requests a stop, or collect the sensor data for a duration specified in the request's parameters.

The sensor data stream can be published as a network accessible stream, for example, as a networked-based API. For example, patient data exchange engine 105 can include an HTTP server and publish the sensor data stream via a web service over HTTP(S). The stream can comprise one or more data files encapsulated within an XML structure (e.g., WSDL, SOAP, proprietary XML, ATOM, RSS, etc.). It should be appreciated that the instantiated stream represents a data conduit through which data is exchanged and that the stream can be treated as a distinct, manageable data object. The stream object can include data members that encode the stream identifier (e.g., GUID, UUID, etc.), stream owner, stream time stamp (e.g., time of creation, time since last data, etc.), patient information if accessible, stream metadata describing the stream (e.g., parameters used to create stream, access levels, etc.), or other factors. These factors or other factors can then be used by computing devices to manage the stream itself.

Sensors 140, 144, 150, 152, 154, and 156 may be configured to monitor and retrieve the sensor data in a default sensor configuration. The default sensor configuration may not satisfy the parameters of the request. In such embodiments, data compilation module 125 may reconfigure at least some of identified sensors 140, 144, 150, 152, 154, and 156 in a new sensor configuration to compile the necessary sensor data for the request. Reconfiguration of sensors 140, 144, 150, 152, 154, and 156 can encompass at least one of the followings: changing the frequency of measuring the body condition (e.g., changing the sampling rate), changing the sensitivity, enabling a sensor reading to be synchronized with another sensor reading (e.g., reading the heart rate and body temperature at the same time, etc.), changing measurement scales, etc.

In some embodiments, if data compilation module 125 determines that the reconfiguration would defeat the original purpose (e.g., the new sensor configuration is in conflict with the default sensor configuration) of an identified sensor, data compilation module 125 may remove such sensor from the identified sensors list. In the event that all sensors are not capable of performing the original purpose in the new sensor configuration, data exchange manager module 110 may reject the request and notify the rejection to the user via user interface 120.

In various embodiments, patient data exchange engine 105 may reconfigure identified sensors 140-160 (e.g., 140, 144, 150, 152, 154, and 156) without disrupting the "normal" operation of the sensors. In some embodiments, patient data exchange engine 105 may instruct the identified sensors to generate sensor data according to the new sensor configuration as well as the default (e.g., previous) sensor configuration. Patient data exchange engine 105 can generate two separate data streams: a first sensor stream that comprises sensor data collected according to the default sensor configuration, which can be provided to a first recipient (e.g., the patient, the patient's primary doctor), and a second sensor stream that comprises sensor data collected according to the new sensor configuration, which can be provided to a second recipient, namely, the user who made the request (e.g., researcher, etc.). In various embodiments, patient data exchange engine 105 ensures that satisfying the requests are performed seamlessly (i.e., transparent to the patients).

After reconfiguring at least some of identified sensors 140, 144, 150, 152, 154, and 156, data compilation module 125 retrieves or receives sensor data from the identified sensors. Data compilation module 125 can store the sensor data as a sensor stream in patient database 135 before providing the user access to the data stream via user interface 120 and client 175. In some embodiments, data compilation module 125 may scrub sensitive information (e.g., identity of the patients) from the sensor data before converting the sensor data into the sensor stream. Data compilation module 125 of some embodiments may aggregate different sensor streams (e.g., that share at least one common patient attribute) into one sensor stream before storage and sending to the user. In some embodiments, data compilation module 125 can provide pre-filtering or pre-analyze the stream, for example, to reduce bandwidth consumption due to reducing the size or composition of the data.

In some embodiments, data exchange manager module 110 may also send the sensor data request to transaction module 130 to enable a transaction based on the request. For example, transaction module 130 may compute a monetary value for the request based on the set of parameters (e.g., demographic information of the patients whose patient data are being requested) in the request. Transaction module 130 may compute a higher monetary value when the demographic attribute of the patients (e.g., ethnicity, age, etc.) is rarer (e.g., for the data requested), and compute a lower monetary value when the demographic attribute of the patients is more common. Transaction module 130 can also compute the monetary value of the request based on a detected health/medical condition of the patients whose patient data are being requested. For example, transaction module 130 may compute a higher monetary value when the medical condition is rarer, and compute a lower monetary value when medical condition is more common. In addition, transaction module 130 can compute the monetary value based on treatment, reaction to a treatment, duration of monitoring the sensor data, other attributes, and a combination of these attributes specified in the request parameters.

Transaction module 130 may enable a transaction with the user with respect to the request based on the monetary value. For example, transaction module 130 can request payment based on the computed monetary value before providing the user access of the data stream in response to the request. In some embodiments, once the transaction is complete, data exchange manager module 110 may play back the data stream. Generating the monetary value for the data streams has several advantages. For example, patients can be paid for providing their healthcare data to one or more research entities, possibly in support of longitudinal studies; a market place of real-time healthcare data can be made available.

An example environment that can be leverage the disclosed techniques include the cOS™ platform such as those offered by Nanthealth (see URL nanthealth.com/cos-clinical-operating-system). For example, the disclosed engines and modules can be integrated into cOS platform as additional services. Example techniques of providing services within cOS platform are described in U.S. Pat. No. 8,689,008, and U.S. pre-grant publications 2011/0313787, 2013/0054272, 2013/0144653, 2013/0166317, 2013/0304512, and 2013/0304496, the disclosures of which are incorporated herein in their entireties.

The patient data services can provide a discovery mechanism through which individuals can provide access to their data as "Me as a Service" or "Patient as a Service". The nature (i.e. metadata describing the type of data available) of the individual's data can be made available without violating the privacy of the patient, assuming validation or authentication requirements have been satisfied. When data requests are fielded, patient data exchange engine 105 can provide a "discovery response" message indicating the nature of the data or services that are available even down to the individual or individual sensor level.

In various embodiments, patient data exchange engine 105 can encrypt the generated data stream before storing the stream in patient database 135 and/or making the stream available for the user. Once the generated data stream has been consumed by the user, patient data exchange engine 105 may remove the sensor stream from patient database 135, for example, for clearing space for newer generated sensor streams.

Figure 3:
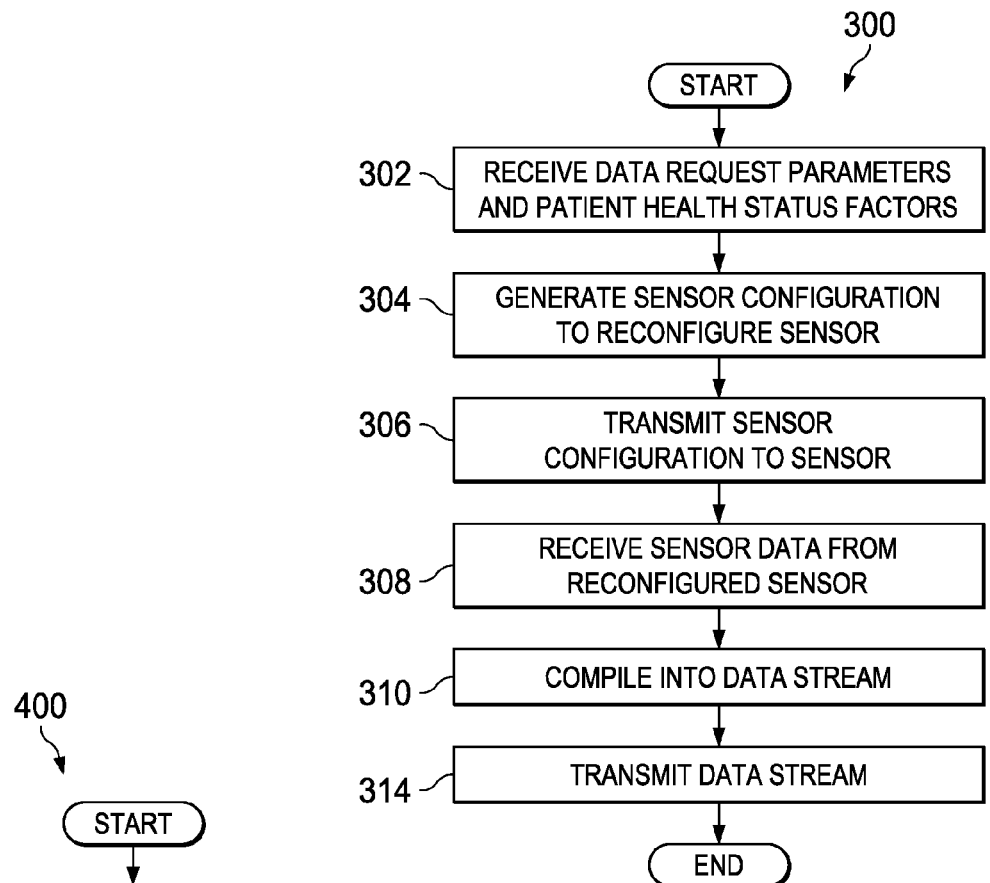
FIG. 3 is a simplified flow diagram illustrating example operations that may be associated with an embodiment of the system.

Turning to FIG. 3, FIG. 3 is a simplified flow diagram illustrating example operations 300 that may be associated with embodiments of system 10. At 302, patient data exchange engine 26 may receive data request parameters 36 and patient health status factors 38. At 304, patient data exchange engine 26 may generate sensor configuration 22 that can reconfigure sensor 12 to generate sensor data 14 that is responsive to data request parameters 36 according to patient health status factors 38. At 306, patient data exchange engine 26 may transmit sensor configuration 22 to sensor 12. At 308, patient data exchange engine 26 may receive sensor data 14 from reconfigured sensor 12 in response. At 310, patient data exchange engine 26 may compile sensor data 14 into a data stream. At 314, patient data exchange engine 26 may transmit the data stream in response to receiving data request parameters 36 and patient health status factors 38.

Figure 4:
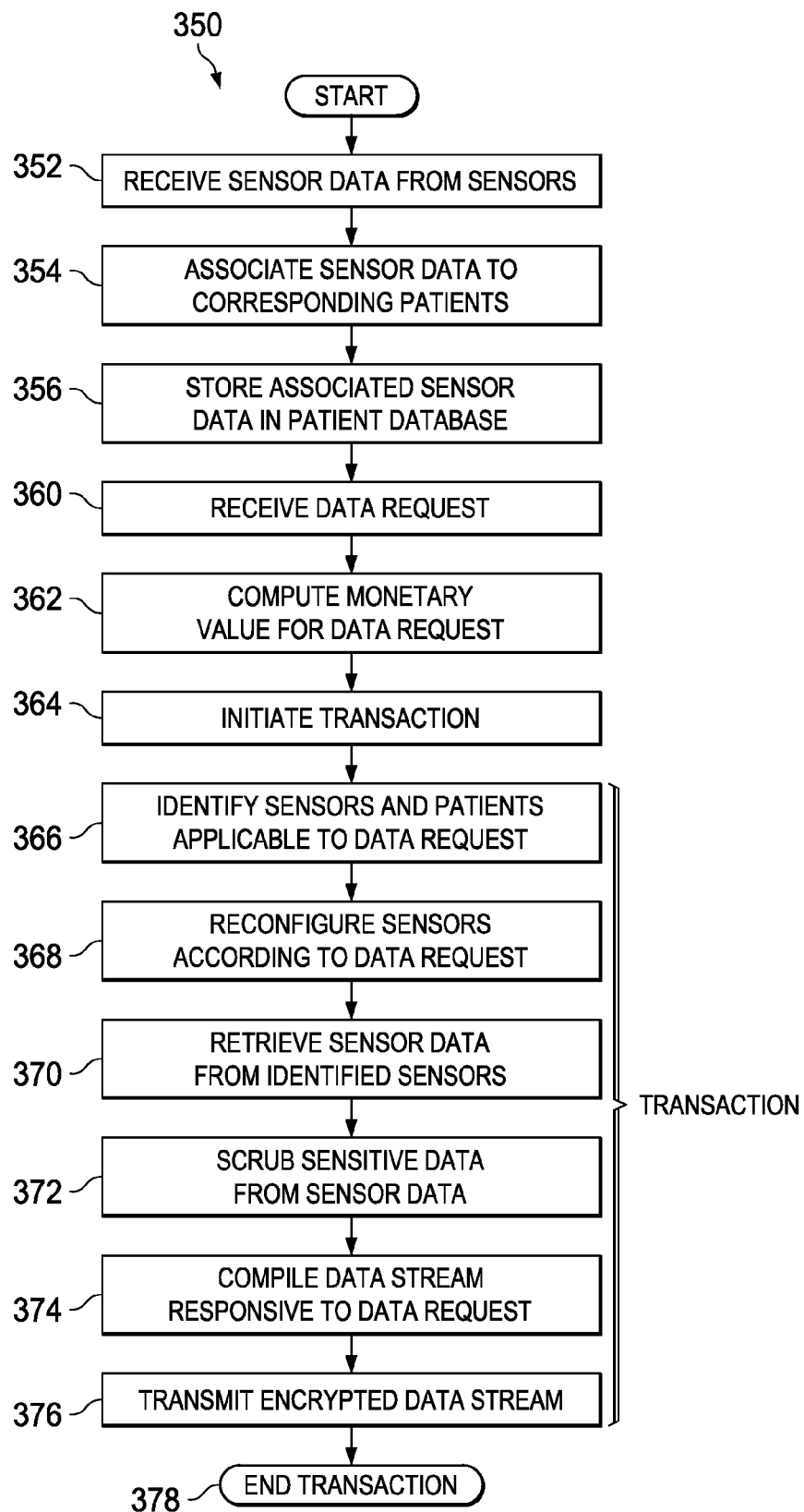
FIG. 4 is a simplified flow diagram illustrating other example operations that may be associated with an embodiment of the system.

Turning to FIG. 4, FIG. 4 is a simplified flow diagram illustrating example operations 350 that may be associated with embodiments of system 100. At 352, patient data exchange engine 105 may receive sensor data from sensors 140-160. At 354, patient data exchange engine 105 may associate the received sensor data to corresponding patients 162-170. The associating may be based on sensor parameters, such as sensor identifier, sensor capabilities, etc. and the patient's health parameters, such as the patient's health conditions, disease, monitored vital signs, etc. For example, sensor 140 may be associated with patient 162 based on the sensor's capabilities—sensor 140 is a heart monitor, and patient 162 suffers from a heart condition. In another example, sensor 142 may be associated with patient 164 based on the locations of sensor 142 and patient 164—they are co-located in the same private hospital room. In yet another example, sensor 148 and patient 164 may be associated based on their respective identifiers—sensor 148 is a wearable medical device that is configured with the patient's name and other identifying information. Various other associating mechanisms may be included within the broad scope of the embodiments. At 356, patient data exchange engine 105 may store the associated data in patient database 135.

At 360, patient data exchange engine 105 may receive a data request from client 175. Merely as an example, and not as a limitation, the data request may request sensor data from all heart monitors that are currently (e.g., as of the time of the data request) measuring patients who have had a heart bypass surgery in the past 5 days in a particular geographic area. In another example, the data request may be for substantially all sensor data related to a specific patient. In yet another example, the data request may request sensor data from all sensors measuring patients in intensive care units of certain hospitals. Virtually any suitable data request for sensor data may be included within the broad scope of the embodiments.

At 362, patient data exchange engine 105 may compute a monetary value for the data request. The monetary value may be determined based on any suitable parameter. In one example embodiment, the monetary value may be based on the scope of the data request, with a larger scope (e.g., larger amount of data) resulting in a higher monetary value. In another example embodiment, the monetary value may be based on the extent of privacy, with highly private data, which is authorized, commanding a higher value than a generic population based low privacy data. In yet another example embodiment, the monetary value may be based on patient health status factors—with rarer health conditions commanding higher monetary value than more common health conditions. In yet another example, the monetary value may be based on the identity of the requester—a patient requesting the patient's own data can have a lower monetary value than a drug company representative requesting access to the patient's data. Virtually any suitable parameter, or set of parameters may be used to compute the monetary value of the data request.

At 364, patient data exchange module 105 may initiate a transaction for the data request. In one example embodiment, initiating the transaction may include creating a secure tunnel for data communication; specifying a payment method; authenticating the payment method; processing payment; etc. At 366, patient data exchange module 105 may identify sensors 140-160 and patients 162-170 that are applicable to the data request. At 368, patient data exchange engine 105 may reconfigure a portion of the identified sensors 140-160 according to the data request. For example, the data request may require reconfiguring the measurement frequency of identified sensors 140-160. In another example, the data request may require reconfiguring the data format of the sensor data of identified sensors 140-160. Virtually any appropriate reconfiguration applicable to the respective sensors may be included within the broad scope of the embodiments.

At 370, patient data exchange engine 105 may retrieve sensor data from identified sensors 140-160. In some embodiments, the sensor data may be retrieved from the reconfigured sensors. In some other embodiments, the sensor data may be retrieved from patient database 135, which is populated by the reconfigured sensors. At 372, patient data exchange engine 105 may scrub sensitive data from the retrieved sensor data. At 374, patient data exchange engine 105 may compile a data stream responsive to the data request from the retrieved sensor data. At 376, patient data exchange engine 105 may transmit the data stream, encrypted as appropriate, in response to the data request. At 378, patient data exchange engine 105 may end the transaction. Ending the transaction may include closing any secure communication tunnels, signing off (or logging off) any authenticated sessions, etc. In various embodiments, operations 366-376 may comprise one or more transactions.

Figure 5:
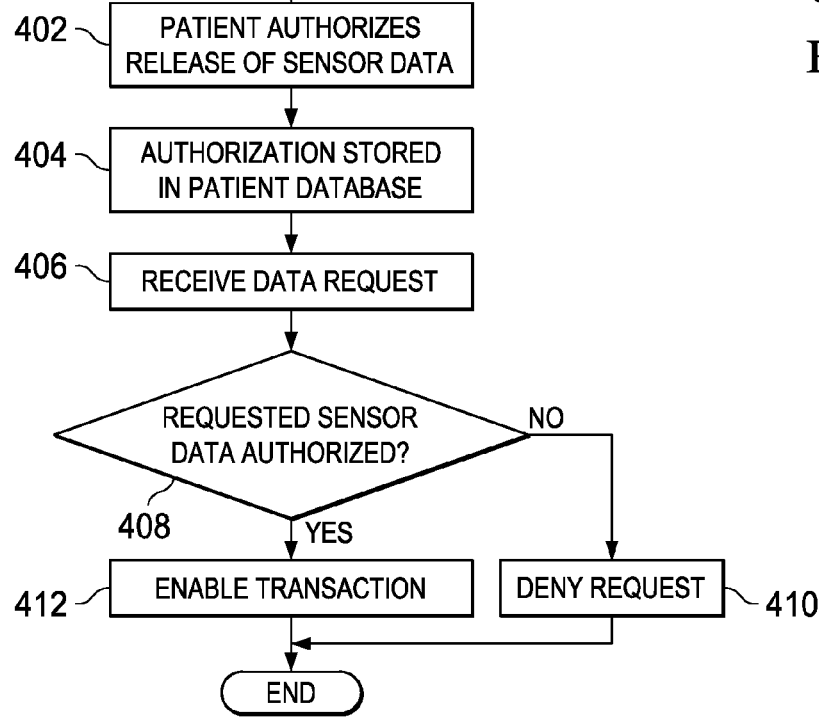
FIG. 5 is a simplified flow diagram illustrating yet other example operations that may be associated with an embodiment of the system according to an embodiment.

Turning to FIG. 5, FIG. 5 is a simplified flow diagram illustrating example operations 400 that may be associated with embodiments of system 10. At 402, a patient may authorize release of sensor data 14. In some embodiments, the patient may authorize the release when (e.g., during, as, etc.) sensor data 14 is collected. In other embodiments, the patient may authorize the release before sensor data 14 is collected. In yet other embodiments, the patient may authorize the release after sensor data 14 is collected. The authorization may be obtained remotely (e.g., via text message, response on a web site, etc.), or may be obtained at sensor 12, or by any other suitable mechanisms. At 404, the patient's authorization may be stored in patient database 34. In some embodiments, the authorization may be associated with substantially all of the patient's data in patient database 34; in other embodiments, the authorization may be associated only with sensor data 14 from a particular sensor 12, or from other sensors. In yet other embodiments, the authorization may be associated with a particular client 18, or recipient, etc.

At 406, patient data exchange engine 24 may receive data request 16, for example, through data request parameters 36 and/or patient health status factors 38. At 408, patient data exchange engine 24 may determine whether the requested data is authorized by the patient. If not authorized, at 410, patient data exchange engine 24 may deny data request 16. If the requested data is authorized, at 412, patient data exchange engine 24 may enable one or more transactions (e.g., see operations 364-378 in previous figure) to provide the requested data.

It should be apparent to those skilled in the art that many more modifications besides those already described are possible without departing from the inventive concepts disclosed herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The foregoing discussion provides many example embodiments of systems and methods for patient sensor data exchanges. Although each embodiment represents a single combination of various elements, all possible combinations of the disclosed elements are intended to be included in the broad scope of the disclosure. Thus if one embodiment comprises elements A, B, and C, and a second embodiment comprises elements B and D, then the scope of the disclosure is considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. Note that any recitation of ranges of values herein is merely intended to serve as a shorthand method of referring individually to each separate value falling within the range. Unless otherwise indicated herein, each individual value is incorporated into the specification as if it were individually recited herein.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. The use of any and all examples, or exemplary language (e.g. "such as") provided with respect to certain embodiments herein is intended merely to better illuminate the invention and does not pose a limitation on the scope of the embodiments otherwise claimed. No language in the specification should be construed as indicating any non-claimed essential.

In example implementations, at least some portions of the activities outlined herein may be implemented in software in, for example, patient data exchange engine 24 or 105. In some embodiments, one or more of these features may be implemented in hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, adapter 16 and various other components described and shown herein (and/or its associated structures) may also include suitable interfaces for receiving, transmitting, and/or otherwise communicating data or information in a network environment. Additionally, some of the processors and memory elements associated with the various nodes may be removed, or otherwise consolidated such that a single processor and a single memory element are responsible for certain activities. In a general sense, the arrangements depicted in the FIGURES may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc. Moreover, all methods described herein can be performed in any suitable order unless otherwise indicated herein or otherwise clearly contradicted by context.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some of example embodiments, one or more memory elements (e.g., memory element 46, databases 20, 34) can store data used for the operations described herein. This includes the memory element being able to store instructions (e.g., software, logic, code, etc.) in non-transitory media such that the instructions are executed to carry out the activities described in this Specification. These devices may further keep information in any suitable type of non-transitory storage medium (e.g., random access memory (RAM), read only memory (ROM), field programmable gate array (FPGA), erasable programmable read only memory (EPROM), EEPROM, etc., software, hardware, or in any other suitable component, device, element, or object where appropriate and based on particular needs.

A processor can execute any type of instructions associated with the data to achieve the operations detailed herein in this Specification. In one example, processors (e.g., processor 44) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

The information being tracked, sent, received, or stored in system 10 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Note also that the disclosed subject matter herein enables construction or configuration of an adapter to operate on digital data (e.g., raw sensor data, alarm condition, sensor configuration, etc.), beyond the capabilities of a human or un-configured (e.g., off-the-shelf) medical device. Although the digital data represents sensor data, it should be appreciated that the digital data is a representation of one or more digital models of a patient's medical measurements (and other indicators) and not the measurements (or indicators) themselves, which comprise activities or operations performed by sensors and/or adapters. By instantiation of such digital models in the memory of the adapter, the adapter is able to manage the digital models in a manner that could provide utility to an individual (e.g., a user of the system) that the individual would lack without such a tool.

It should also be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, random access memory (RAM), flash memory, read-only memory (ROM), etc.). The software instructions can configure a suitable computing device to provide the roles, responsibilities, or other functionality as discussed herein with respect to the disclosed apparatus. In some embodiments, the various servers, systems, databases, or interfaces exchange data using standardized protocols or algorithms, possibly based on hyper-text transfer protocol (HTTP), hyper-text transfer protocol secure (HTTPS), Advanced Encryption Standard (AES), public-private key exchanges, web service application programming interfaces (APIs), known financial transaction protocols, or other electronic information exchanging methods. Data exchanges preferably are conducted over a packet-switched network, the Internet, local area network (LAN), wide area network (WAN), virtual private network (VPN), or other type of packet switched network.

As used in the description herein and throughout the claims that follow, when a system, engine, server, device, module, or other computing element is described as configured to perform or execute functions on data in a memory, the meaning of "configured to" or "programmed to" refers to one or more processors or cores of the computing element being programmed by a set of software instructions stored in the memory of the computing element to execute the set of functions on target data or data objects stored in the memory.

One should appreciate that the disclosed techniques provide many advantageous technical effects including reduction in latency between a computing device ingesting healthcare data and generating a prediction or recommendation. Latency is reduced through storage of health care data in a memory and in the form of N-grams, which can be computationally analyzed quickly.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, system 10 may be applicable to other exchanges or routing protocols. Moreover, although system 10 has been illustrated with reference to particular elements and operations that facilitate the communication process, these elements, and operations may be replaced by any suitable architecture or process that achieves the intended functionality of system 10.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) or (f) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. An apparatus comprising:
   a non-transitory, computer readable memory storing software instructions that comprises a patient data exchange engine; and
   a processor coupled with the memory wherein the processor, upon execution of the software instructions, performs operations comprising:
   communicating with a clinical operating system (cOS) executing in a remote server in a network;
   communicating with a plurality of sensors coupled to the apparatus, wherein each of the plurality of sensors monitors a patient according to a first sensor configuration;
   receiving, from the cOS, a request from a client in the network for patient sensor data associated with a patient health status, the patient health status comprising one or more health status parameters;
   receiving, from the cOS, patient health status factors associated with the plurality of patients;
   identifying a sensor from among the plurality of sensors based on the one or more health status parameters and the patient health status factors;
   generating a second sensor configuration based on the request, the second sensor configuration being different from the first sensor configuration; and
   reconfiguring the identified sensor according to the second sensor configuration.

2. The apparatus of claim 1, further configured for:
   receiving the sensor data from the reconfigured sensor; and
   transmitting the received sensor data to the cOS, wherein the cOS forwards the received sensor data to the client.

3. The apparatus of claim 1, wherein the apparatus associates the sensor data with the patient and stores the associated sensor data in a patient database.

4. The apparatus of claim 1, wherein the first sensor configuration comprises a time-synchronization with another of the plurality of sensors.

5. The apparatus of claim 1, wherein the identified sensor generates patient sensor data at a first sampling rate according to the first sensor configuration, wherein the patient data exchange engine further reconfigures the identified sensor to have a second sampling rate according to the one or more parameters.

6. The apparatus of claim 1, wherein the patient data exchange engine further reconfigures the identified sensor to remove an identifier associated with the patient from the sensor data according to the one or more parameters.

7. The apparatus of claim 1, wherein the patient data exchange engine further rejects the request if reconfiguring the identified sensor defeats an original purpose of the identified sensor.

8. The apparatus of claim 1, wherein the patient data exchange engine further computes a monetary value for generated sensor data based at least on an attribute of the patient and an attribute of the sensor data.

9. The apparatus of claim 8, wherein the patient data exchange engine further enables a transaction with respect to generated sensor data using the computed monetary value.

10. The apparatus of claim 8, wherein the patient data exchange engine further computes the monetary value based on a rarity of the attribute among a plurality of patients.

11. The apparatus of claim 8, wherein the attribute of the patient comprises a demographic attribute of the patient.

12. The apparatus of claim 8, wherein the attribute of the patient comprises a health condition of the patient.

13. The apparatus of claim 12, wherein the health condition comprises at least one of a disease, a treatment, and a reaction to a treatment.

14. The apparatus of claim 8, wherein the attribute of the patient comprises a location of the patient.

15. The apparatus of claim 1, wherein the patient data exchange engine aggregates multiple streams of the sensor data that are associated with a plurality of patients sharing at least one attribute.

16. The apparatus of claim 1, wherein the patient data exchange engine provides a user access to generated sensor data.

17. The patient data exchange system of claim 16, wherein the patient data exchange engine further scrubs the generated sensor data to remove any information that can identify the patient before providing the user access to the generated sensor data.

18. The patient data exchange system of claim 16, wherein the patient data exchange engine further compresses the generated sensor data before providing to the user.

19. The patient data exchange system of claim 1, wherein the patient data exchange engine further:

derives a patient health attribute from the generated sensor data responsive to the request;

determines a rarity of the patient health attribute among a plurality of patients;

derives a correlation between the patient health attribute and the at least one health status parameter of the request; and computes a monetary value for the request based on the determined rarity and the correlation.

20. A method comprising:

communicating with a clinical operating system (cOS) executing in a remote server in a network;

communicating with a plurality of sensors, wherein each of the plurality of sensors monitors a patient according to a first sensor configuration;

receiving, from the cOS, a request from a client in the network for patient sensor data associated with a patient health status, the patient health status comprising one or more health status parameters;

receiving, from the cOS, patient health status factors associated with the plurality of patients;

identifying a sensor from among the plurality of sensors based on the one or more health status parameters and the patient health status factors;

generating a second sensor configuration based on the request, the second sensor configuration being different from the first sensor configuration; and reconfiguring the identified sensor according to the second sensor configuration.

21. A non-transitory program storage medium on which are stored instructions executable by a processor or programmable circuit to perform operations comprising:

communicating with a clinical operating system (cOS) executing in a remote server in a network;

communicating with a plurality of sensors, wherein each of the plurality of sensors monitors a patient according to a first sensor configuration;

receiving, from the cOS, a request from a client in the network for patient sensor data associated with a patient health status, the patient health status comprising one or more health status parameters;

receiving, from the cOS, patient health status factors associated with the plurality of patients;

identifying a sensor from among the plurality of sensors based on the one or more health status parameters and the patient health status factors;

generating a second sensor configuration based on the request, the second sensor configuration being different from the first sensor configuration; and reconfiguring the identified sensor according to the second sensor configuration.

* * * * *